United States Patent [19]
Fuller

[11] Patent Number: 5,516,633
[45] Date of Patent: May 14, 1996

[54] DNA SEQUENCING WITH A T7-TYPE GENE 6 EXONUCLEASE

[75] Inventor: Carl W. Fuller, Cleveland Heights, Ohio

[73] Assignee: Amersham Life Science, Inc., Cleveland, Ohio

[21] Appl. No.: 927,562

[22] Filed: Aug. 6, 1992

Related U.S. Application Data

[63] Continuation-in-part of Ser. No. 745,193, Aug. 15, 1991.

[51] Int. Cl.$^6$ .............................. C12Q 1/68; C12P 19/34; C07H 21/04
[52] U.S. Cl. ........................... 435/6; 435/91.2; 435/91.5; 436/94; 536/24.33; 935/17; 935/77; 935/78
[58] Field of Search .................. 435/6, 91, 91.5, 435/91.2; 536/27, 23.1, 25.3, 24.33; 935/77, 78; 436/94

[56] References Cited

FOREIGN PATENT DOCUMENTS

| | | |
|---|---|---|
| 9105061 | 4/1991 | WIPO . |
| 9105060 | 4/1991 | WIPO . |
| 9106678 | 5/1991 | WIPO . |

OTHER PUBLICATIONS

Prober et al Science (1987) 238:336–341.
Straus et al Bio Techniques (Mar. 1991) 10:376–384.
Shon et al. J Biol Chem (1982) 257:13823–13827.
Kerr et al. J. Biol Chem 1972 247:305–310.
Kerr et al. J. Biol Chem 1972 247: 311–318.
Ott et al Bio Chemistry 1987 26:8237–8241.
Oste et al. Bio techniques (1988) 6: 162–167.
Sayers et al., 16 *Nucleic Acids Research* 791, 1988, "5'–3' Exonucleases in Phosphorothioate–based Oligonucleotide Directed Mutagenesis".
Oste, 6 *BioTechniques* 162, 1988, "Polymerase Chain Reaction".
Prober et al., 238 *Science* 336, 1987, "A System for Rapid DNA Sequencing with Fluorescent Chain–Terminating Dideoxynucleotides".
Shon et al., 257 *J. Biol. Chem.* 13823, 1982, "The Nucleotide Sequence of the Replication Origin β of the Plasmid R6K".
Straus et al., 10 *BioTechniques* 376, 1991, "In Vitro Production of Large Single–Stranded Templates for DNA Sequencing".
Higuchi and Ochman, 17 *Nucleic Acids Research* 5865, 1989, "Production of Single–stranded DNA templates by exonuclease digestion following the polymerase chain reaction".
Kerr et al., 247 *J. Biol. Chem.* 311, 1972, "Gene 6 Exonuclease of Bacteriophage T7; II; Mechanism of the Reaction".
Zagursky et al., *Genome Mapping and Sequencing* 198, 1990.
Bastia et al., 78 *Proc. Natl. Acad. Sci. USA* 2095, 1981, "The Nucleotide Sequence Surrounding the Replication Terminus of R6K".
Smith, 6 *Nucleic Acids Research* 831, 1979, "The Use of Exonuclease III for Preparing Single Stranded DNA for Use as a Template in the Chain Terminator Sequencing Method".

Primary Examiner—W. Gary Jones
Assistant Examiner—Carla Meyers
Attorney, Agent, or Firm—Lyon & Lyon

[57] ABSTRACT

Method for determining the nucleotide base sequence of DNA present in a lambda virus coat which is not replicable in a bacterial cell independent of any lambda DNA within that coat. The method includes preparing a lambda phage preparation containing the DNA, purifying the nucleic acid from the lambda phage to provide purified nucleic acid, and contacting that purified nucleic acid with a T7-type gene 6 exonuclease to allow the exonuclease to remove at least a portion of one strand of the DNA. The method further includes providing a primer able to hybridize with the other strand of the DNA complementary to the portion of the one strand and contacting the primer with the other strand of DNA in the presence of at least one deoxynucleoside triphosphate (dNTP) and at least one chain terminating agent (e.g., a dideoxynucleoside triphosphate, ddNTP) and a DNA polymerase, to allow the primer to be extended by the polymerase until extension is stopped by incorporation of the chain terminating agent.

1 Claim, 16 Drawing Sheets

BOTH STRANDS DEGRADED TO HALF-LENGTH.
SEQUENCING OF HALF OF EACH STRAND POSSIBLE

ONE STRAND FULLY DEGRADED, ONE INTACT.
FULL LENGTH OF INTACT STRAND CAN BE SEQUENCED.

DNA SEQUENCING WITH A T7-TYPE GENE 6 EXONUCLEASE

BACKGROUND OF THE INVENTION

This application is a continuation-in-part of Fuller, U.S. Ser. No. 07/745,193, filed Aug. 15, 1991, hereby incorporated by reference herein. This invention relates to methods for sequencing of linear double-stranded DNA molecules in which the DNA is made single stranded by use of an exonuclease.

The sequence of nucleotide bases in a DNA molecule can be determined in a variety of ways. The chain termination method generally involves synthesizing DNA, complementary to the template strand to be sequenced, by extending a primer able to hybridize to a portion of that template strand, with a DNA polymerase. During the synthesis reaction, deoxynucleoside triphosphates (dNTPs) are incorporated to form a DNA fragment until a chain terminating agent, for example, a dideoxynucleotide triphosphate (ddNTP) is incorporated. Incorporation of a ddNTP prevents further DNA synthesis (a process called chain termination). The size of each DNA fragment synthesized in this procedure is then determined by gel electrophoresis, and this information used to determine the sequence of nucleotides in the original template DNA. For example, Tabor and Richardson, U.S. Pat. No. 4,795,699, describe a two step sequencing method in which an unlabelled primer is labelled in a labelling step, and then extended in the presence of an excess of four dNTPs and a ddNTP in a chain termination step. In the labeling step a low concentration of dNTPs is provided (one being labelled) to allow a small amount of primer extension.

In order to sequence double stranded DNA molecules using a chain termination sequencing technique, the double stranded DNA must be made single stranded. In general, this is achieved by denaturing the DNA molecule with either heat or alkali, or by use of an enzyme, such as an exonuclease, which selectively removes one of the strands of DNA. For example, Bastia et al., 78 *Proc. Natl. Acad. Sci USA* 2095, 1981, Shon et al., 257 *Journal of Biological Chemistry* 13823, 1982, and Smith, 6 *Nucleic Acid Research* 831, 1979, describe use of T7 gene 6 exonuclease and exonuclease III for sequencing plasmid DNA. In this method, the plasmid is linearized with a restriction endonuclease and then separately treated with either one of the 5' or 3' exonucleases. The resulting single stranded DNA is then sequenced.

Zagursky et al., *Genome Mapping and Sequencing* 198, 1990, describe use of 3'- or 5'-exonucleases for sequencing plasmid DNA. Similarly, Straus and Zagursky, 10 *BioTechniques* 376, 1991 (which is not admitted to be prior art to the present application) describe sequencing of plasmids or cosmids with either T7 gene 6 exonuclease or exonuclease III.

Higuchi and Ochman, 17 *Nucleic Acid Research* 5865, 1989, describe use of lambda exonuclease to produce single stranded DNA from polymerase chain reaction (PCR)-amplified DNA. That is, DNA is produced by extension of two primers complementary to opposite strands of the nucleic acid to be amplified to form two complementary strands which hybridize together. This hybridized DNA is then denatured and the primers again extended on the resulting single-stranded fragments. These two steps are then repeated 15–30 times, to produce a large quantity of amplified DNA.

SUMMARY OF THE INVENTION

The present invention provides a method for sequencing lambda and PCR-generated linear DNA molecules, and for sequencing double-stranded DNA molecules using fluorescent labels. The method surprisingly provides excellent results compared to prior methods for sequencing such DNA molecules.

Applicant has discovered that the gene product (an exonuclease) of a T7-type gene 6 (that is, a phage from the T7 family of phages., e.g., T7, T3, ΦI, ΦII, H, W31, gh-1, Y, A1122, or SP6 gene products), is particularly useful for DNA sequencing. This exonuclease is readily inactivated by heat; thus, the exonuclease activity can be removed without extensive purification of the DNA. The exonuclease also has activity on DNA with either 5'-hydroxyl or 5'-phosphoryl termini, and will readily degrade DNA which has 5'-recessed, blunt or 5'-protruding ends. It has a high rate of degradation, and possesses no detectable endonuclease or single-strand exonuclease activities. The method is most useful in sequencing plasmid DNA with fluorescent labels in which data equivalent to that obtained with M13 single-stranded DNA can be achieved, i.e., 400–500 bases with greater than 99% accuracy. Further, the method is the most reliable presently available method for sequencing lambda DNA. For PCR-produced DNA the method allows use of the same primers used to generate the PCR-produced DNA. The method is relatively fast, in that sequencing can be achieved in about thirty minutes, and the reagents commonly used for sequencing are compatible with the method.

Thus, in a first aspect, the invention features a method for determining the nucleotide base sequence of a linear duplex DNA molecule (e.g., one present in a lambda virus coat, which is not replicable in a bacterial cell independent of the lambda DNA within that coat, or produced by amplification, e.g., by a polymerase chain reaction). The method includes, consists of, or consists essentially of, contacting the DNA with a T7-type gene 6 exonuclease to allow the exonuclease to remove at least a portion of one strand of the DNA. The method further includes providing a primer, able to hybridize with the other strand of the DNA complementary to a portion of the one strand, and contacting the primer with the other strand of DNA in the presence of at least one (preferably four) deoxynucleoside triphosphate (dNTP), at least one chain terminating agent (e.g., a dideoxynucleoside triphosphate, ddNTP), and a DNA polymerase, to allow the primer to be extended by the polymerase until extension is stopped by incorporation of the chain terminating agent.

Thus, for example this method features sequencing of lambda DNA molecules in which the lambda DNA is replicable within any standard *E. coli* host. Such a DNA molecule does not include a cosmid or related vector.

In a second related aspect, the invention features a method for determining the nucleotide base sequence of double stranded DNA in which the DNA to be sequenced is contacted with a T7-type gene 6 exonuclease, as discussed above, and the primer, or the chain terminating agent (or even a dNTP), is labelled with a fluorescent label.

By fluorescent label is meant any of a number of chemical moieties which can be chemically attached to a sequencing primer or dideoxynucleotide, and which fluoresce when irradiated by ultra-violet or visible light. Examples include fluorescein, rhodamine, NBD (7-nitrobenzo-2-oxa-1,3-diazole) and their derivatives. These are chemically attached to sequencing primers by several methods, see, e.g., Smith et al. 13 *Nucleic Acids Research* 2399, 1985; Ansorge et al., 15 *Nucleic Acids Research* 4593, 1987; Brumbaugh et al., 85 *Proc. Natl. Acad. Sci.* 5610, 1988; and Kambara et al. 6 *Bio/Technology* 816, 1988. They can also be chemically attached to a chain-terminating nucleotide (e.g., a dideoxynucleotide, Prober et al., 238 *Science* 336, 1987, and Bergot et al., WO 91/05060. Other fluorescent labels include dansyl (5-(dimethylamino)napthalene-1-sulfonate), mansyl (6-(N-methylanilino)-naphthalene-2-sulfonate) and bimanes, see, e.g., Allen et al. 28 *Biochemistry* 4601, 1989; Fidanza & McLaughlin, 111 *J. Am. Chem. Soc.* 9117, 1989; and Hodges et al. 28 Biochemistry 261, 1989.

This invention solves the problem of creating a suitable single-stranded sequencing template from a linear duplex DNA. This duplex DNA, such as the DNA extracted from bacteriophage lambda, can be readily denatured (either by heating or by treatment with NaOH), but such denaturation is readily reversible under the solution conditions normally used for annealing a primer, and performing a sequencing reaction. Annealing of the primer is in competition with re-annealing of the template during the time required to complete the sequencing reaction.

Sequencing bacteriophage lambda DNA using published procedures (Manfiolette et al., 16 *Nucleic Acids Research* 2873, 1988; and Kim et al., 8(2) BioTechniques 156, 1990) produces significantly inferior results compared to the present invention. The autoradiograms are usually blank or extremely faint, yielding unreliable sequence data. It appears that insufficient primer/template is available for sequencing when the primer is simply mixed with the lambda DNA template, heated and quickly cooled. While the use of more template might overcome this problem (and indeed does for smaller linear double-stranded DNAs), bacteriophage lambda DNA is so large that it is not possible to use enough DNA in practice.

T7 gene 6 exonuclease has a non-processive 5'–3' exonuclease activity which degrades only double-stranded DNA (Kerr et al., 247 *J. Biol. Chem.*, 305, 1972; Kerr et al., 247 *J. Biol. Chem* 311, 1972; and Thomas and Olivera 253 *J. Biol. Chem.* 424, 1978). When a linear DNA is exhaustively treated with this enzyme, the products consist of single-stranded DNA molecules. This is analogous to, but in the opposite direction from the action of exonuclease III. Exonuclease III, however, acts relatively slowly, requiring many hours to hydrolyze a DNA as large as the chromosome of bacteriophage lambda (Bastia et al., 78 *Proc. Nat'l Acad. Sci. USA* 2095, 1981). Furthermore, exonuclease III has significant endonuclease and other interfering activity when used at high concentration and it is difficult to inactivate by heating such that unreliable results are obtained (Rogers et al., 65 *Methods in Enzymology* 201, 1980). In contrast, linear single- and double-stranded DNAs can be treated with large excesses of this enzyme with no evidence of further degradation. Digestion of bacteriophage lambda DNA can be completed in 10–30 minutes, and the exonuclease can be inactivated by heating briefly at 65° C. The present procedure is simple, rapid, relatively inexpensive, and is readily automated. Thus, it is a useful alternative for sequencing DNA cloned in bacteriophage lambda vectors.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 5A:
Figure 5B:
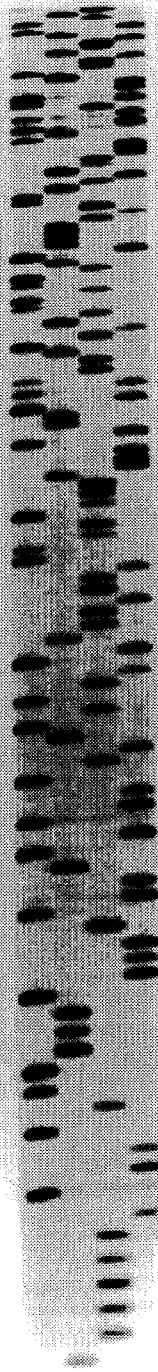
Figure 5C:
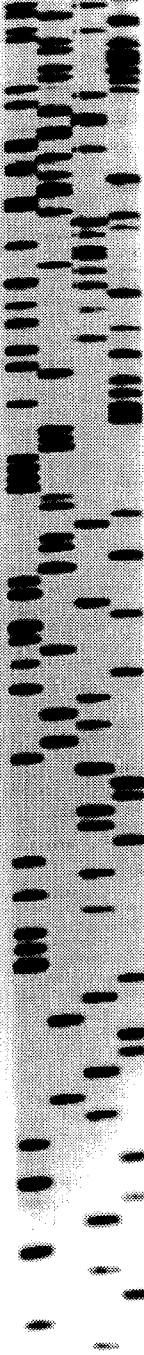
Figure 6A:
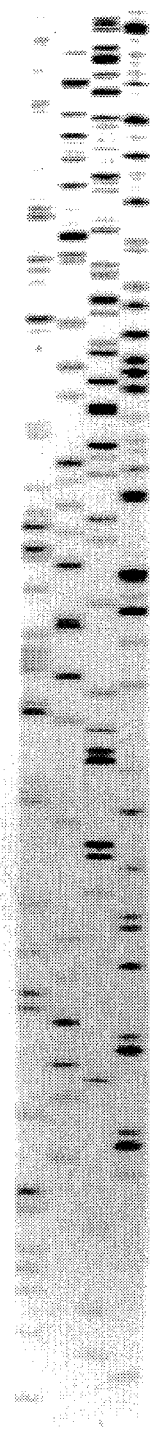
Figure 6B:
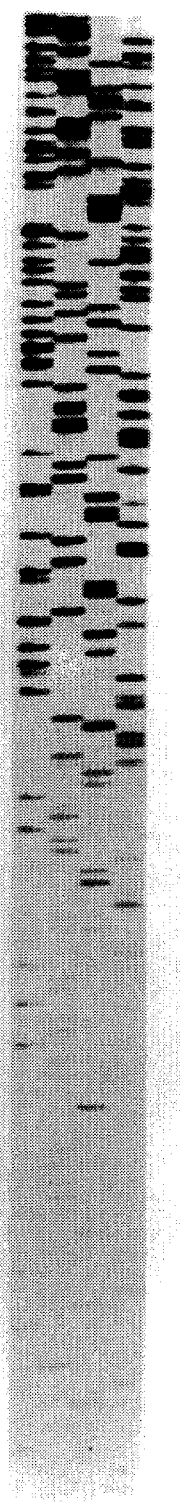
Figures 7A, 7B:
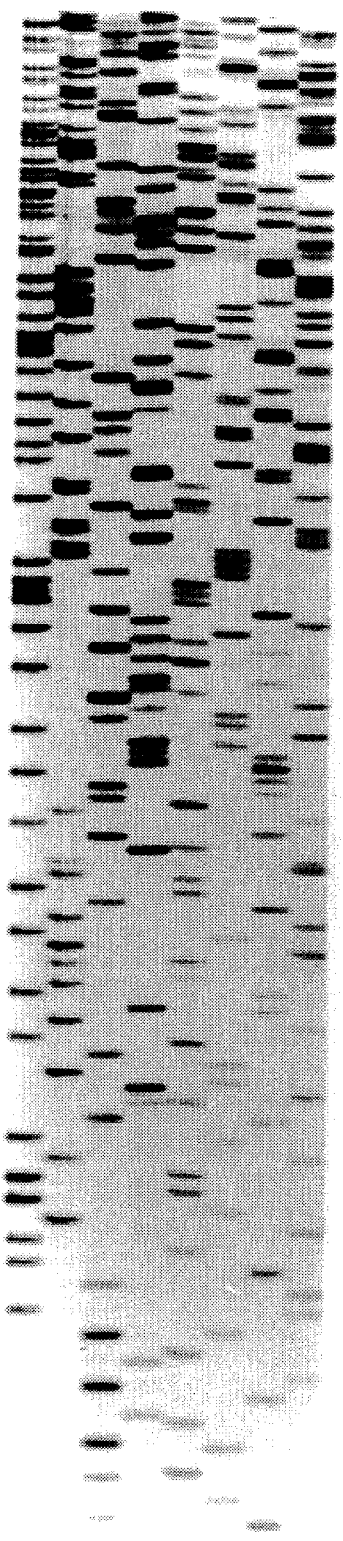
Figure 8:
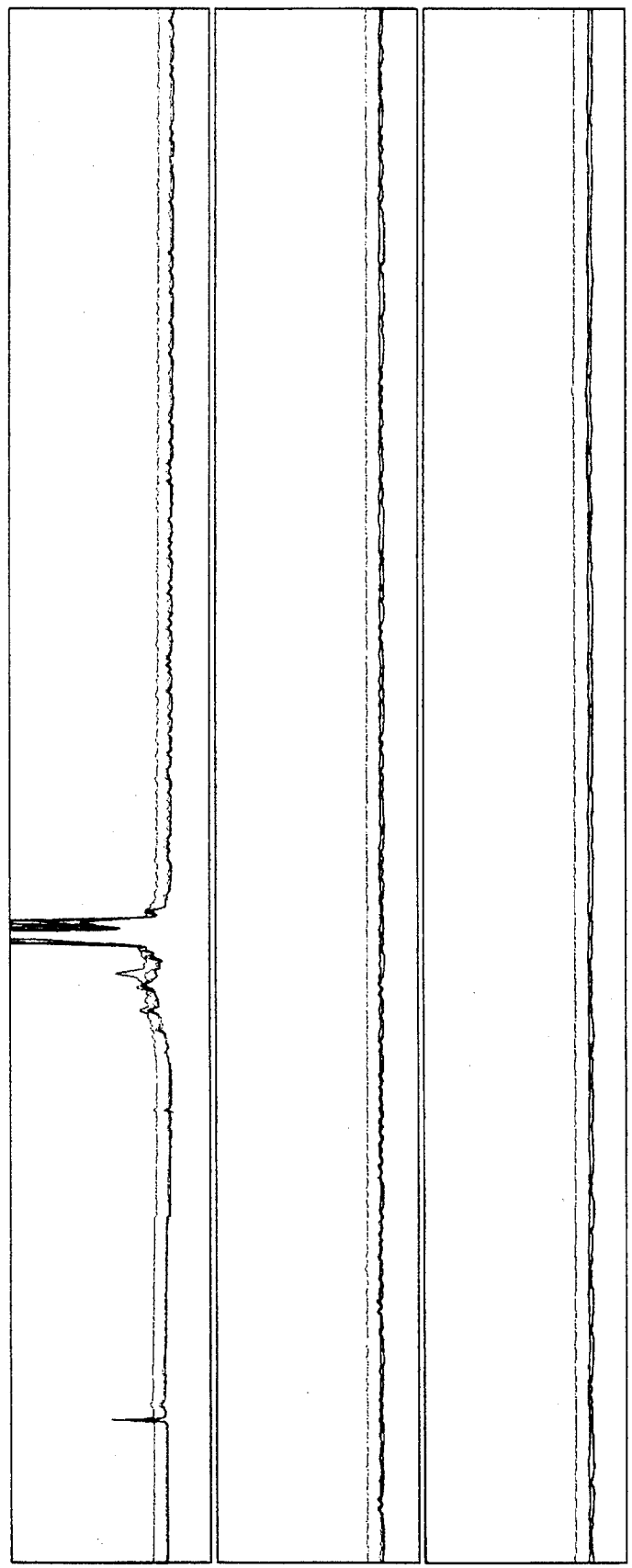
Figure 8:
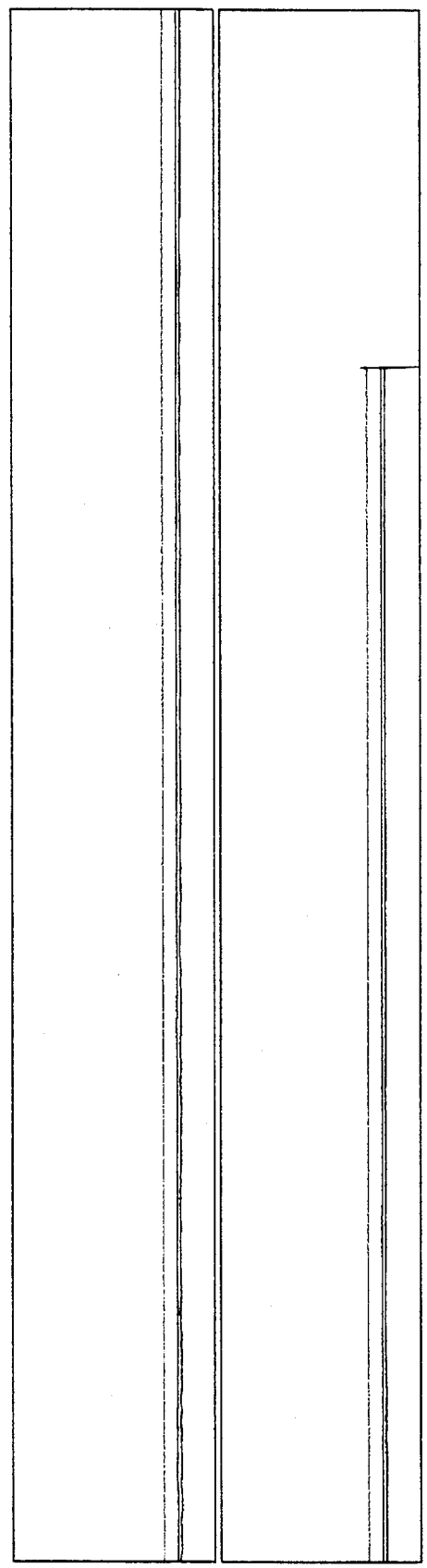
Figure 9:
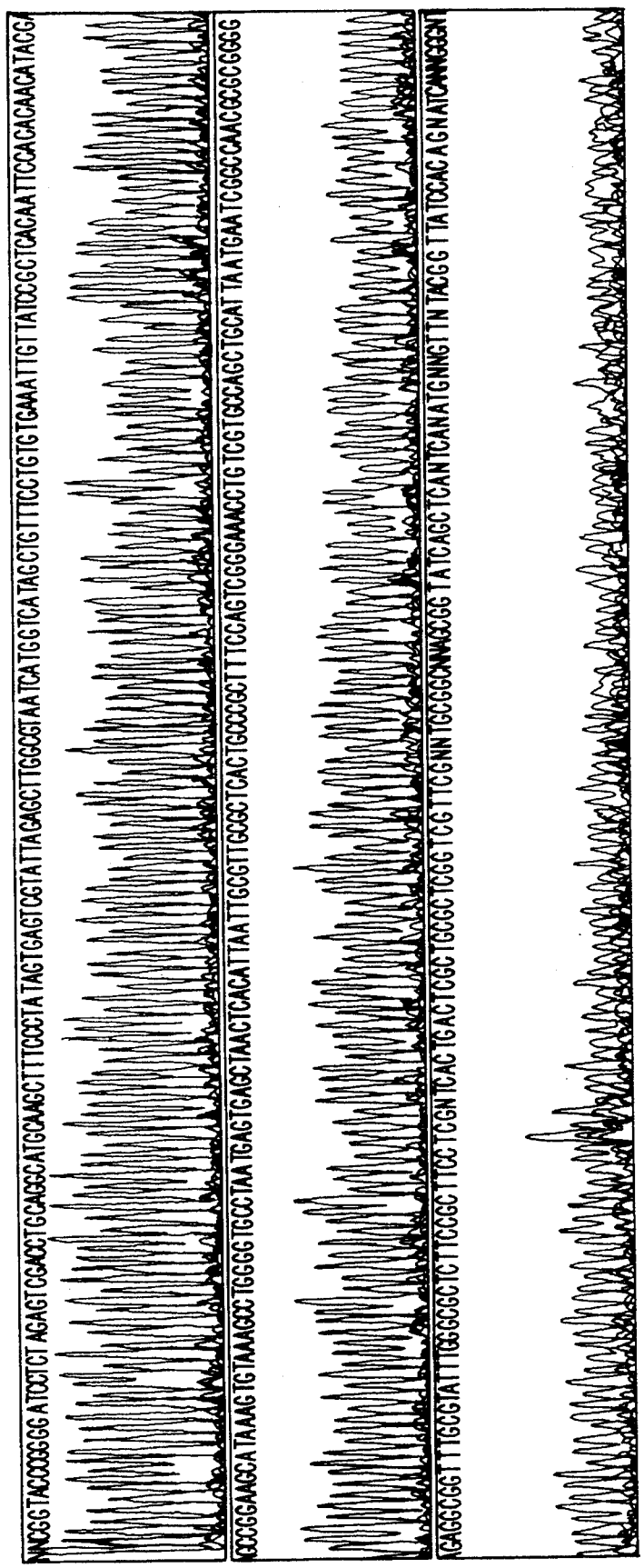
Figure 10:
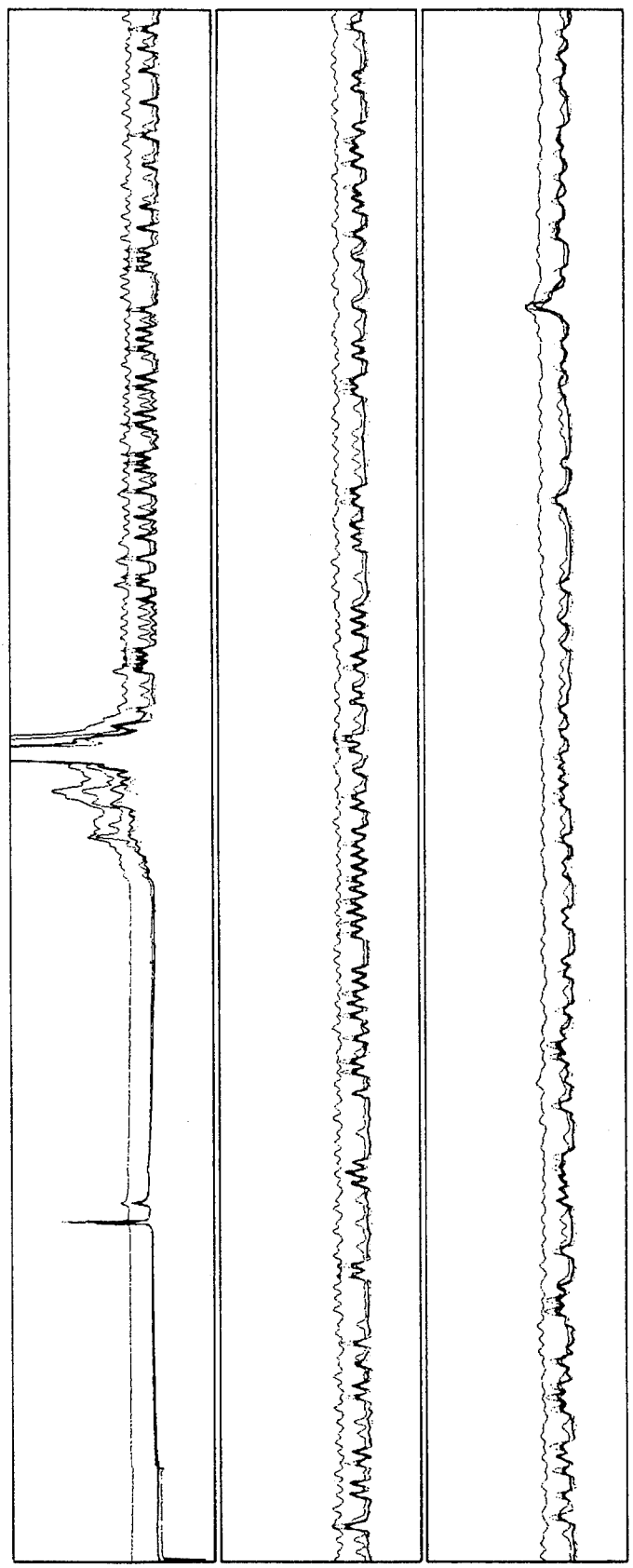
Figure 10:
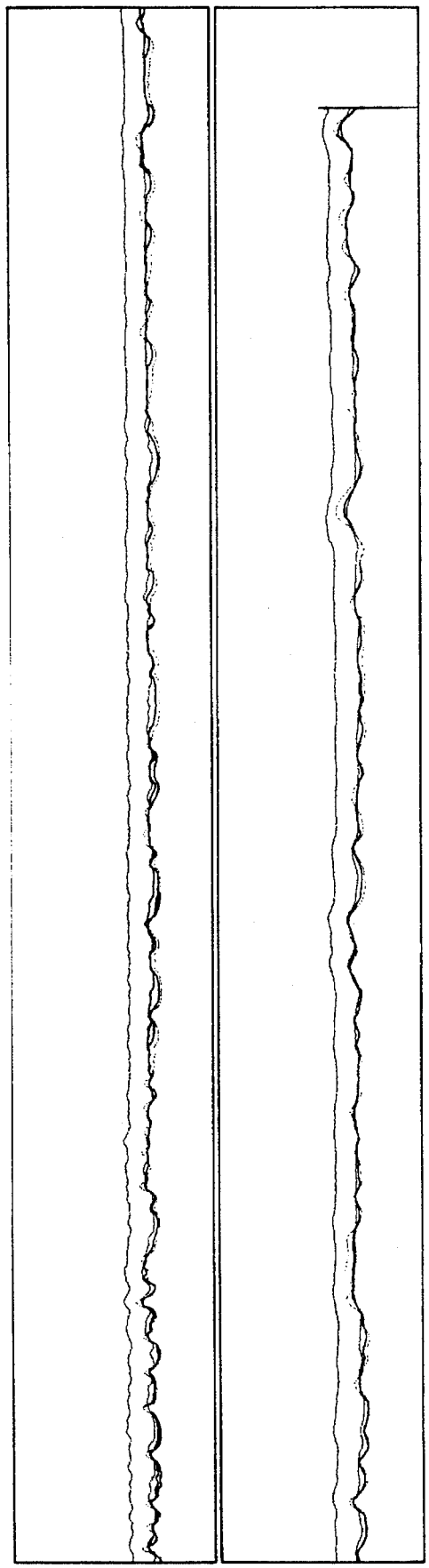
Figure 11:
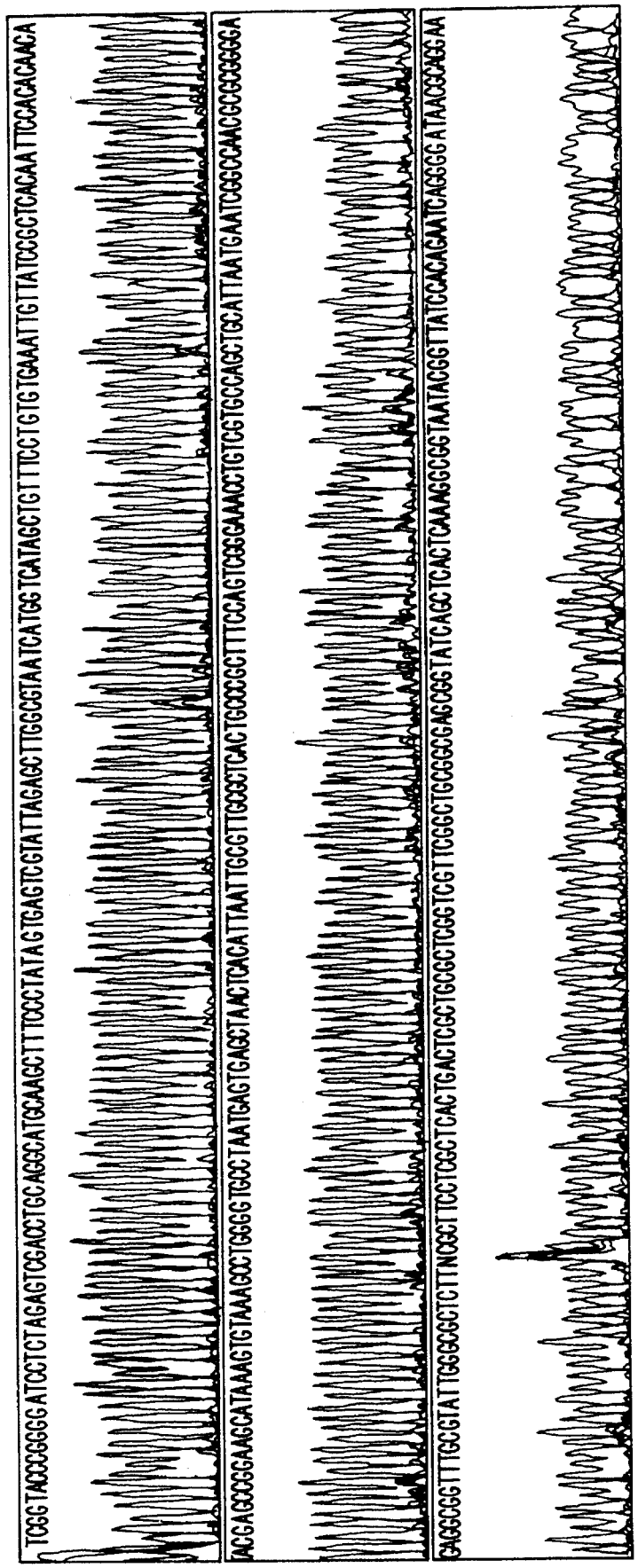
Figure 11:
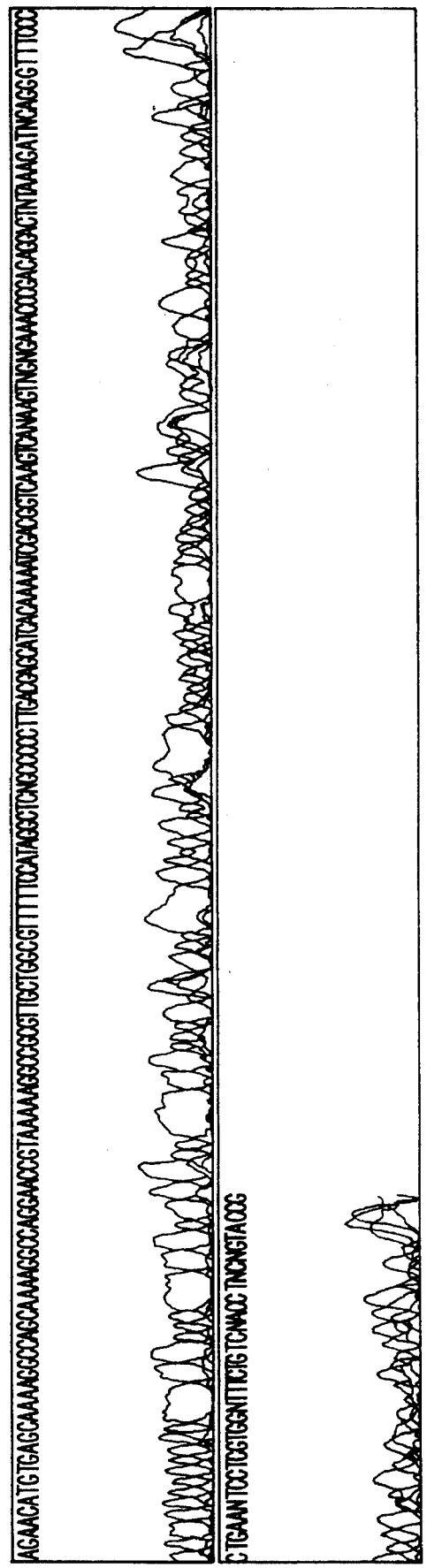
Figure 12A:
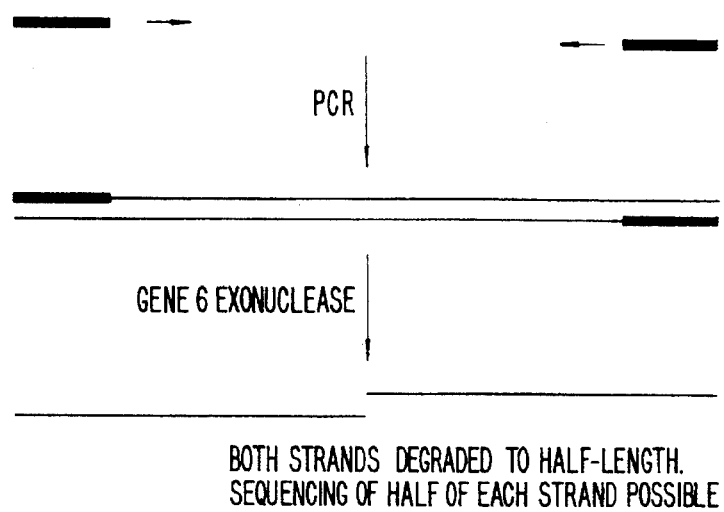
Figure 12B:
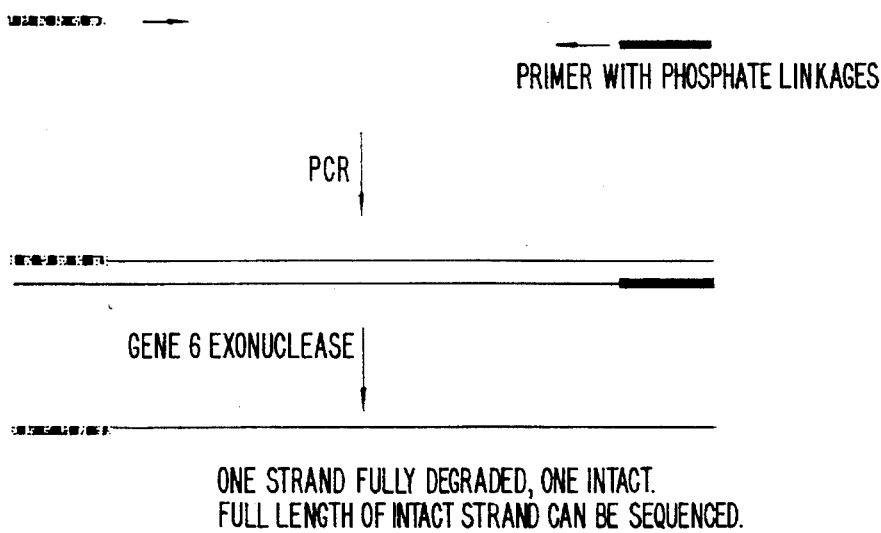

FIGS. 5A, 5B, and 5C are copies of autoradiograms showing sequencing results with undigested lambda DNA (5A), or digested with EcoRI (5B and 5C) using two different primers;

FIGS. 6A and 6B are copies of autoradiograms showing sequencing results from DNA digested with KpnI (FIG. 6A) or SacI (FIG. 6B);

FIGS. 7A and 7B are copies of autoradiograms showing sequencing results of PCR-generated DNA from lambda (FIG. 7A) or phage M13 (FIG. 7B);

FIGS. 8 and 10 are copies of results of sequencing reactions obtained by use of an Applied Biosystems Instrument using alkali (FIG. 8) or gene 6 exonuclease (FIG. 10) to digest the DNA;

FIGS. 9 and 11 are copies of results obtained by analysis of FIGS. 8 and 10 respectively, using a standard procedure, the sequences of which are provided as Sequence ID Nos. 1 and 2, below; and FIGS. 12A and 12B are diagrammatic representations of a PCR using primers with phosphate and phosphorothioate linkages, respectively.

METHODS

Figure 1:
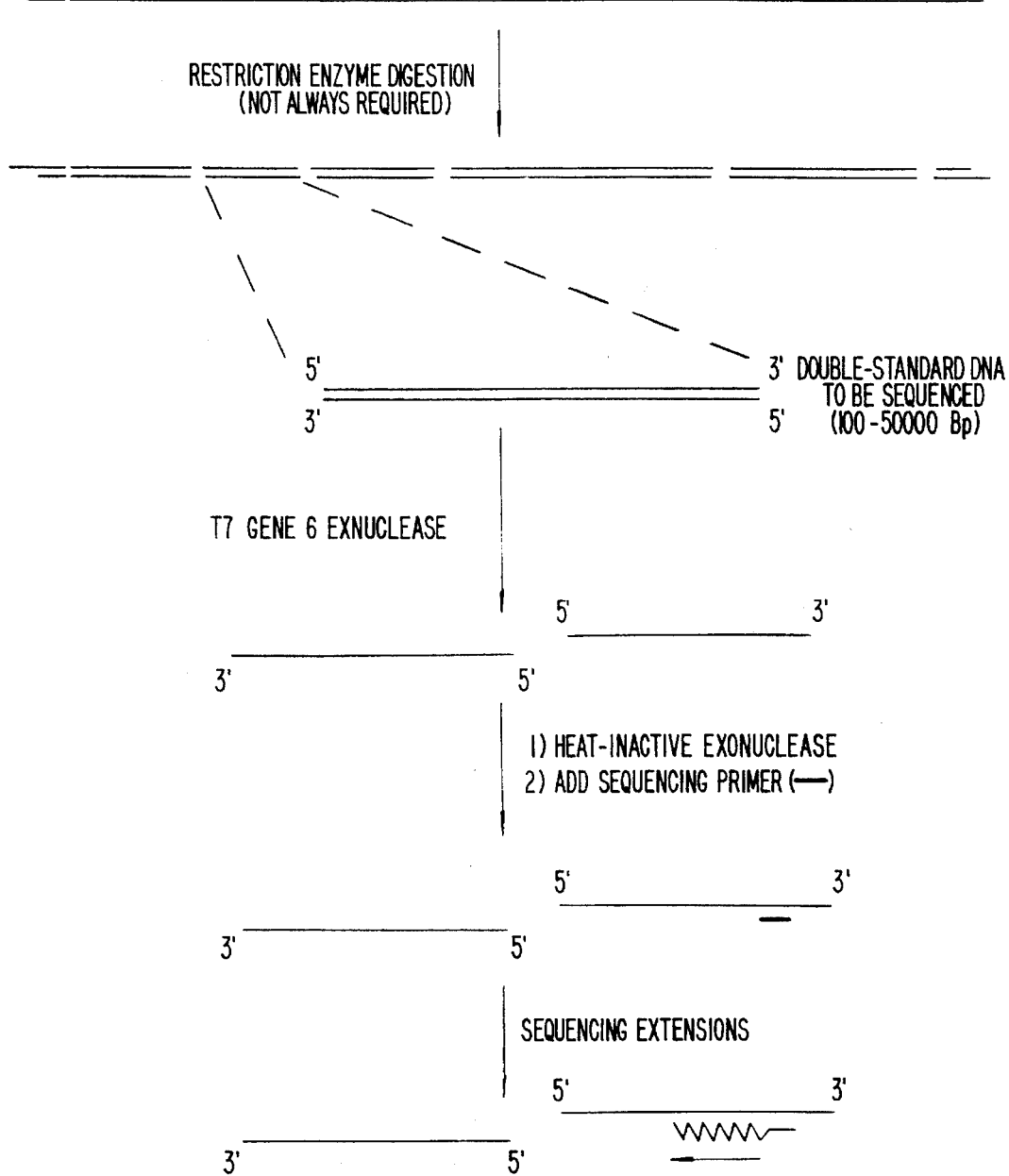
FIG. 1 is a schematic representation of a method for sequencing lambda DNA.

Referring to FIG. 1, the overall scheme for sequencing lambda DNA is shown. The first step is to cleave the lambda DNA with a restriction enzyme which cleaves near the desired sequencing priming site (but not within the sequence to be determined). This step is optional for sequencing DNA in the left half of the chromosome using the bottom strand (the strand oriented 3'–5', left to right as illustrated in the Figure) as template. Restriction endonuclease cleavage is, however, required for sequencing the same region using the top strand as template, as shown in FIG. 1. Better results are usually obtained from either strand if the DNA is first cut with a restriction enzyme, perhaps because bacteriophage lambda DNA usually has several "nicks" randomly distributed along its length.

The DNA is next treated with gene 6 exonuclease, generating single-stranded DNA molecules. (While all of the restriction fragments will be degraded by the exonuclease, only one (the one with the sequencing priming site) is shown in the figure.) The resultant single-stranded DNA is then annealed to the sequencing primer and used for sequencing in exactly the same manner as single-stranded M13 templates. This entire process, including digestion with the restriction enzyme, the exonuclease and the sequencing reactions can be completed in 1–1.5 hours. A single buffer is used and no precipitation or purification steps are required.

There follow examples of methods for sequencing using T7 gene 6 exonuclease. These examples are not limiting in the invention and those of ordinary skill in the art will recognize that many of the components may be readily substituted by equivalent components. In these examples, the following general protocols were used unless specifically stated otherwise.

Lambda DNA Sequencing

Lambda DNA was prepared at a concentration of 2.5 µg/µl. This was done by ethanol precipitation with at least 75% recovery. A volume containing 0.5 pmol of DNA (about 15 µg) was added to 0.1 volumes 3M sodium acetate (pH5–7), and 2 volumes 95% ethanol, and mixed and chilled (−20° C.) for 1 hour. The DNA was precipitated by centrifugation and washed (70% ethanol), dried, and resuspended in 6 µl of TE (Tris 10 mM, EDTA 1 mM, pH 7.5) buffer.

For restriction endonuclease digestion, 6 µl of DNA (2.5 µg/µl for lambda DNA) was added to 3 µl 5X sequencing buffer (250 mM NaCl, 200 mM Tris-HCl pH 7.5, 100 mM MgCl$_2$); 50 units restriction enzyme (e.g., BglII) added, and water to a total volume of 15 µl. The mixture was incubated for 1 hour at the appropriate temperature (usually 37° C.).

For digestion with T7 Gene 6 Exonuclease 75 Units Gene 6 Exonuclease was added to the above mixture (15 µl) and incubated at 37° C. for 15–30 minutes, and then incubated at 80° C. for 10–15 min. to inactivate the exonuclease. The product was checked on an agarose gel.

For DNA sequencing, a suitable sequencing primer (0.5–1.0 pmol) was added and sequencing reactions run exactly as for M13 DNA using the reagents from the SEQUENASE® DNA sequencing kit (U.S. Biochemical Corporation, Cleveland, Ohio, containing a T7 DNA polymerase and necessary buffers and reagents for DNA sequencing).

Plasmid DNA Sequencing

Plasmid DNA was prepared at a concentration of at least 0.3 µg/µl, e.g., by ethanol precipitation as above. The DNA was restriction endonuclease digested as above, and digested with exonuclease as above using 10 units in place of 75 units. Sequencing was also performed as above.

For sequencing using the ABI model 373A DNA sequencing instrument, the reagents (including fluorescently labeled primers) from the USB/ABI dye-primer sequencing kit were used. Sequencing with this instrument required approximately twice as much template DNA.

PCR-Generated DNA Sequencing

DNA from one, two or more PCR reactions (100 µl, GENEAMP™ Protocols) was purified using a USBIOCLEAN™ glass adsorption kit, redissolved in 10 µl, and digested with 5 units T7 Gene 6 Exonuclease as above. A suitable sequencing primer (0.5–1.0 pmol) was then added. This can be one of the primers used in the PCR process. Sequencing reactions were run exactly as for M13 DNA using the reagents from the SEQUENASE® DNA sequencing kit (U.S. Biochemical Corporation).

EXAMPLE 1

Gene 6 Exonuclease Digestion

Figure 2:
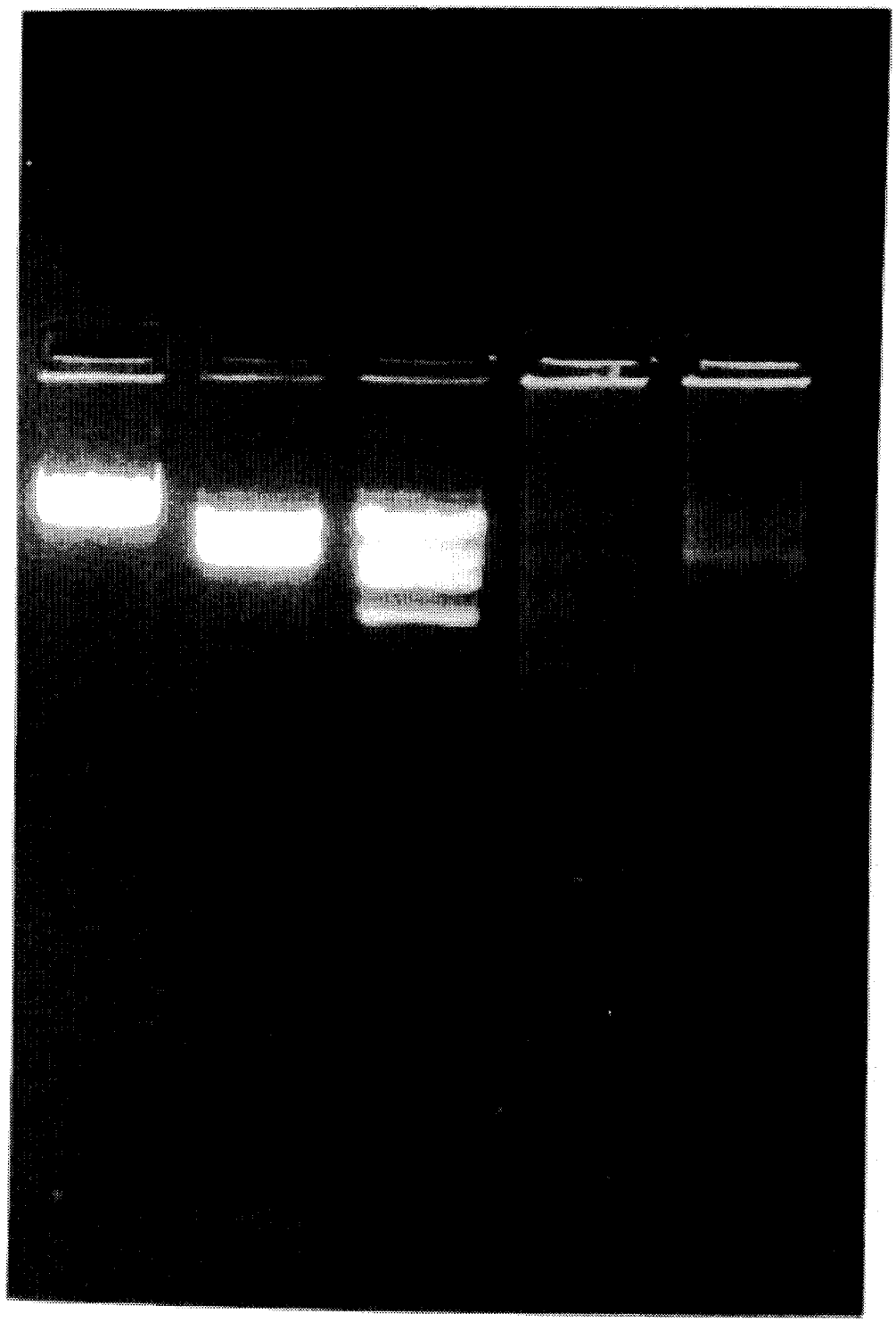
FIG. 2 is a copy of a photograph of an agarose gel showing lambda DNA products before and after T7 gene 6 exonuclease digestion.

Referring to FIG. 2, an agarose gel displaying the products of various of the above steps is shown. This is an agarose electrophoresis gel showing the products of digestion of bacteriophage lambda DNA with BglII, or HindIII and gene 6 exonuclease. Specifically, bacteriophage lambda DNA (vector gt10, 1 µg) was digested with 15 units of either BglII or HindIII at 37° C. for one hour in reaction buffer (250 mM NaCl, 200 mM Tris-HCl pH 7.5, 100 mM MgCl$_2$). Two samples were further digested with 10 units of T7 gene 6 exonuclease at 37° C. for 30 minutes. DNA samples were applied to an agarose gel (0.8%) as follows: lane A, uncut gt10 DNA; lane B, BglII cut DNA; lane C, HindIII cut DNA; lane D, BglII and T7 gene 6 exonuclease cut DNA; lane E, HindIII and T7 gene 6 exonuclease cut DNA.

The large, single-stranded DNA products are poorly resolved and poorly stained on this non-denaturing gel, but it is easy to see that digestion has occurred. One reason for the smeared appearance of the digested DNA may be that the original lambda DNA has one or more randomly placed nicks in each molecule. Digestion of smaller DNAs (such as cut plasmid DNA) reveals that the exonuclease digestion yields relatively sharp, discrete bands of single-stranded DNA.

EXAMPLE 2

Exonuclease Concentration

Figure 3:
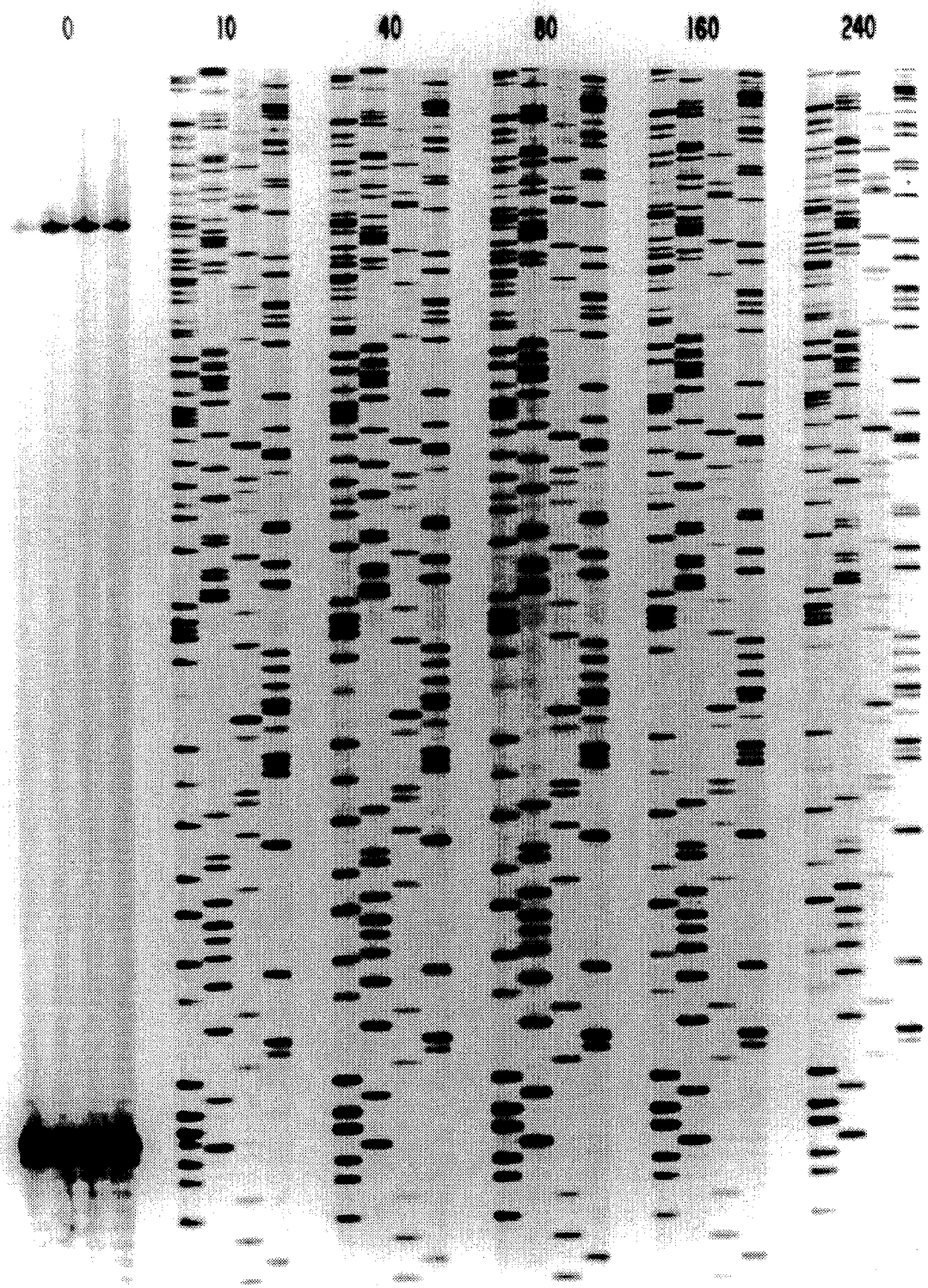
FIG. 3 is a copy of an autoradiogram of a sequencing gel using varying amounts of gene 6 exonuclease in the reaction mixes.

Referring to FIG. 3, the results of sequencing experiments using bacteriophage lambda DNA digested with BglII and gene 6 exonuclease are shown. This shows the effects of varying amounts of T7 gene 6 exonuclease for creating single-stranded sequencing templates from bacteriophage lambda DNA.

Specifically, DNA from bacteriophage lambda (CI$_{857}$ S$_{am7}$) (15 µg) was digested with 25 units BglII at 37° C. for 30 minutes in sequencing buffer. This treatment was followed by digestion with varying amounts of T7 gene 6 exonuclease (0–240 units) as noted in FIG. 3. at 37° C. for 15 minutes. The exonuclease was inactivated by heating at 80° C. for 15 minutes and the DNA sequenced using a SEQUENASE® Version 2.0 DNA sequencing kit (U.S. Biochemical Corporation) and 1.0 pmol of a primer which has the sequence of nucleotides 7131–7155 of bacteriophage lambda. Exonuclease digestion is required for sequencing, but there is little difference in the quality of sequences obtained over the range of 40–240 units. The largest amount of exonuclease used in this experiment (240 units) is enough to digest ten times more DNA than is actually present in the reaction mixture. Thus, the exonuclease digestion step can be run to completion without concern about over-digestion.

EXAMPLE 3

DNA Concentration

It is important to use sufficient template for sequencing reactions. When sequencing bacteriophage M13 DNA, good results are obtained using 1 µg of template DNA and overnight exposure of the autoradiogram. This amount of M13 DNA is approximately 0.5 pmol of template molecules. The chromosome of bacteriophage lambda has a molecular weight approximately 15 times greater than M13. Thus, to achieve similar sequencing performance, it should be necessary to use as much as 15 µg of lambda to obtain good sequences. This is confirmed by the experiment shown in FIG. 4.

Figures 4A, 4B:
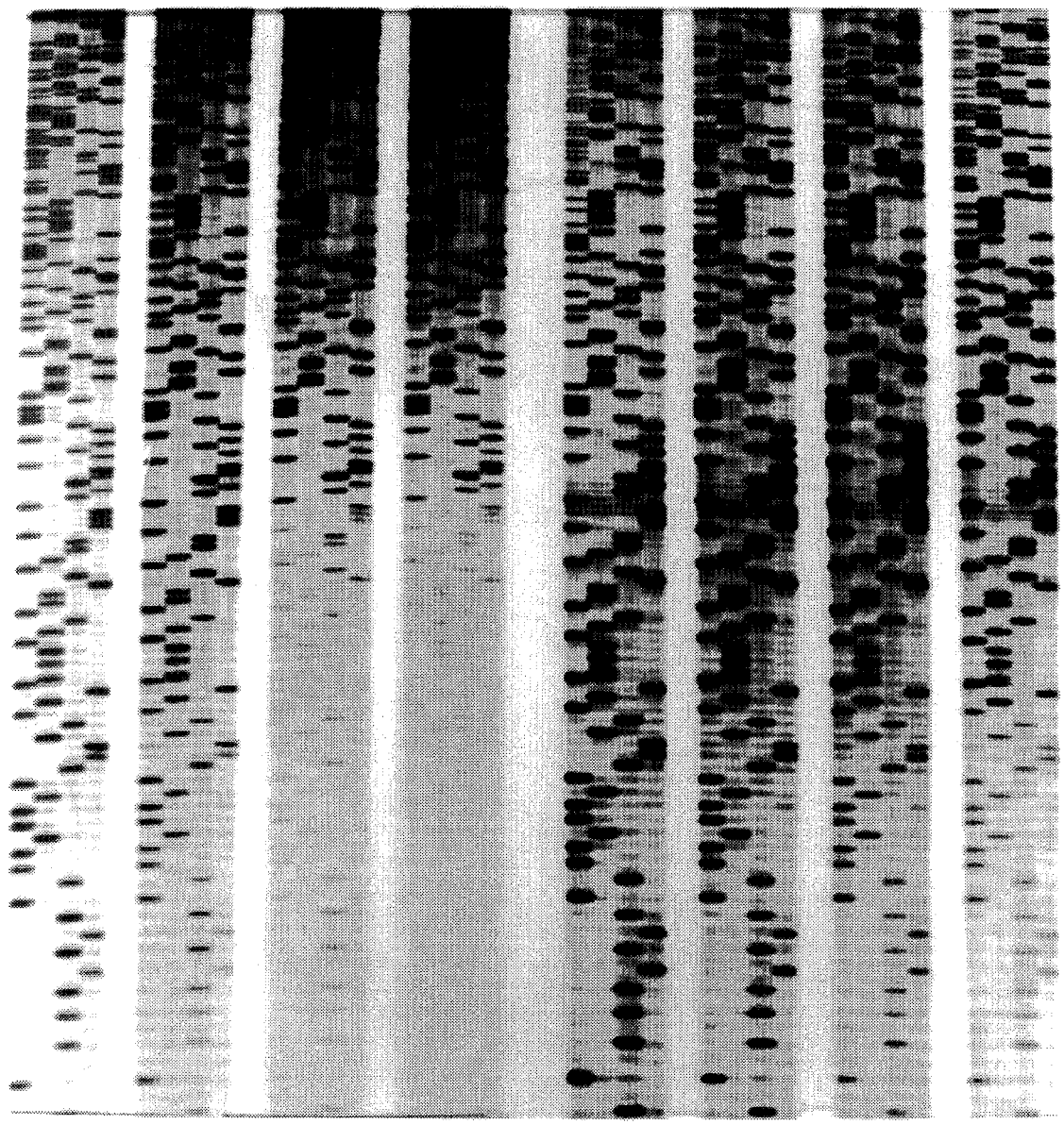
FIGS. 4A and 4B are copies of autoradiograms of sequencing gels using $Mg^{2+}$ or $Mn^{2+}$ buffers, respectively, and various amounts of lambda DNA.

Referring to FIGS. 4A and 4B, sequencing experiments were run as above using the indicated amount of template DNA, and 1.6 units T7 gene 6 exonuclease for each 1.0 µg of DNA. In FIG. 4A, sequences were obtained using Mg$^{2+}$ buffer from the above-noted SEQUENASE® sequencing kit. When following the protocol for sequencing with the SEQUENASE® DNA sequencing kit, 15 µg or more of lambda DNA is required to read sequence within about 15 bases of the 3'-end of the primer. With less DNA, bands representing bases close to the primer are too faint to read.

In FIG. 4B, sequences were obtained using the $Mn^{2+}$ buffer for the SEQUENASE® sequencing kit to compensate for the small amount of template present. When this buffer is used, as little as 3 µg of single-stranded bacteriophage lambda DNA template can be used to read the first 150–200 nucleotides from the priming site. This may be particularly useful since it is sometimes cumbersome to purify large quantities of lambda DNA at high concentration.

Sequencing was also performed using reagents containing dITP and 7-deaza-dGTP, and using pyrophosphatase (not shown). Both analogs of dGTP were effective in resolving compressions, and pyrophosphatase restored weak band intensities when using dITP.

EXAMPLE 4

Restriction Endonuclease Digestion

Since a variety of restriction enzymes might be used for creating the proper single-stranded templates from lambda DNA, a number of restriction enzymes were used to cut the DNA prior to digestion with gene 6 exonuclease. This is of particular interest since exonuclease III does not digest DNA which has a 3'-single-stranded terminus such as the 4-base "overhang" produced by digestion with PstI (Rogers et al., 65 *Methods in Enzymology* 201, 1980, and Henikoff, 28 *Gene* 351, 1984).

Referring to FIG. 5, the sequencing results when the DNA is either digested with EcoRI, which (like BglII) leaves a 4-base single-stranded 5' terminus, or not digested at all, retaining the natural 12-base 5' cohesive ends are shown. The sequence in FIG. 5A was obtained by treating 15 µg intact DNA with 80 units of T7 gene 6 exonuclease 30 min. The primer was the same as for FIG. 3. The sequences in FIG. 5B and FIG. 5C were obtained by digesting the DNA with EcoRI site at nucleotide 21227. The sequence in FIG. 5C was primed using a 26-mer which primes just to the right of the same cleavage site.

Even the 12-base single-stranded ends do not prevent digestion by gene 6 exonuclease to form a single-stranded sequencing template. This is convenient since it ensures that one strand of the sequence of interest can always be sequenced without digestion by a restriction enzyme. Other restriction enzymes which have been used successfully include KpnI, SacI, BglI and HindIII.

EXAMPLE 5

Sequencing Lambda DNA

A practical application of sequencing lambda DNA is shown in FIG. 6. FIG. 6 shows sequences of cDNA cloned in the lambda gt11 vector. The DNA was cleaved with KpnI (A) or SacI (B), and digested with T7 gene 6 exonuclease. Sequences were primed with specific internal primers which anneal at opposite ends of the insert DNA. Sequences were obtained using a purified plate-lysate preparation of the DNA (Sambrook et al., *Molecular Cloning*, Cold Spring Harbor Laboratory Press, Second Edition, p. 2.73–2.81, 1989).

EXAMPLE 6

Sequencing PCR-generated DNA

The above method was tried on the double-stranded product of a polymerase chain reaction. The reaction products were purified using the USBIOCLEAN™ glass adsorption method, digested with gene 6 exonuclease, heated to inactivate the nuclease and sequenced using either of the primers used for PCR.

Referring to FIG. 7A, PCR was performed using bacteriophage lambda DNA and the control primers in the GENEAMP™ DNA amplification kit (Cetus Corp.). The product DNA was purified using a USBIOCLEAN™ kit, treated with T7 gene 6 exonuclease (5 units, 10 minutes), heated 10 minutes at 70° C., and sequenced using one of the PCR primers (PCR01).

Referring to FIG. 7B, PCR was performed using M13mp18 DNA, M13 reverse sequencing primer, and an 18-mer primer which anneals at and adjacent nucleotide 6853. The DNA was treated as above.

The results are excellent and the procedure again is quick and simple. Since double-stranded DNA is directly converted to single-stranded DNA with no tendency to re-anneal, all of the template can be primed and used for the chain-termination sequencing reactions. This procedure for producing single-stranded DNA allows sequencing using methods which have been well-established for sequencing single-stranded DNA.

EXAMPLE 7

Sequencing Plasmid DNA Using Fluorescent Labels

When used for fluorescent sequencing, the above method offers the advantage of greatly improved signal strength and improved sequence accuracy. The results shown in FIGS. 8–11 were obtained using an Applied Biosystems Fluorescent DNA Sequencing Instrument (Model 373A). Four separate sequencing reactions were run using four distinctly labeled fluorescent primers (FAM, JOE, TAMRA and ROX) and one of the dideoxy nucleoside triphosphates.

The specific protocol followed is identical to that described in a 1991 manual for the ABI/USB SEQUENASE Dye-Primer DNA Sequencing Kit (ABI product number 401117). Briefly, in reaction buffer (40 mM MOPS, pH 7.5, 50 mM NaCl, 10 mM $MgCl_2$, 5 mM $MnCl_2$, 15 mM isocitrate) a total of 0.8 pmole (2 µg) of M13mp18 DNA was combined in four annealing reactions (0.1 pmole in each of the A and C reactions, 0.3 pmole in each of the G and T reactions) with one of the four dye-labeled primers using 0.4 pmol primer for the A and C reactions, and 0.8 pmol of primer for the G and T reactions. The reaction mixtures were annealed by heating at 65° C. for 2 min. and slow cooling to <30° C. (about 35 min.). Then, termination mix (dNTPs and one ddNTP) was added to each reaction vial (1 µl to the A and C reactions; 2 µl to the G and T reactions, respectively). Reaction vials were warmed at 37° C., and SEQUENASE® Version 2.0 T7 DNA polymerase and pyrophosphatase added to each vial (2.2 units polymerase, and 0.01 units pyrophosphatase to each of the A and C reactions, and 4.4 units polymerase, and 0.02 units pyrophosphatase to each of the G and T reactions, respectively). Reactions were incubated for 30 min. at 37° C. The four reaction mixtures for each sequence were combined into one vial with 15 µl of Stop/Salt solution (1M NaOAc, 20 mM EDTA), and 180 µl of 95% ethanol. After 15 min. at −20° C., the precipitated DNA was collected by centrifugation (12,000xg) for 15 min., and washed twice with 70% ethanol (repeating centrifugation). The precipitated DNA was vacuum dried, and resuspended in 5 μl of deionized formamide, 8.3 mM EDTA and heated at 95° C. for 2 min. The denatured DNA was applied to 6% polyacrylamide denaturing gel mounted in the Model 373A DNA sequencing instrument. Electrophoresis was conducted at a constant 35W and 42° C. for about 14 hours.

The sequence shown in FIGS. 8 and 9 was obtained using a common technique in which the plasmid template was denatured with alkali prior to sequencing. Specifically, 5 μg of pTZ19R DNA was mixed with 1/10 volume of 2M NaOH and incubated 20 min. at 37° C. (to denature). The mixture was neutralized with 1/10 volume of 3M Sodium Acetate (pH 8.0) and precipitated with 3 volumes of 95% ethanol. After 15 min. at −20° C., the precipitated DNA was collected by centrifugation at 12,000xg for 15 min. and washed twice with 70% ethanol. The DNA was dried under vacuum and redissolved in 16 μl of TE buffer (10 mM Tris-HCl, pH 7.5, 1 mM EDTA). This template then was sequenced using the standard protocol.

The sequence shown in FIGS. 10 and 11 was obtained using 5 μg of pTZ19R DNA. The DNA was first cut with restriction endonuclease NaeI followed by digestion with T7 gene 6 exonuclease (25 units) as described above. After heat treatment to inactivate the exonuclease, the DNA was sequenced using the method provided in the manual for single-stranded M13 DNA (without alkaline denaturation).

Comparison of the results in FIGS. 8 and 10 shows that the signal intensity obtained with gene 6 treatment is 5–7 times greater than that obtained by simple denaturation, although the same amount of template DNA was used. The sequences interpreted by the instrument (FIGS. 9 and 11) are similar for the first 300–320 nucleotides, but the accuracy (and signal intensity) diminishes beyond this point in the case of alkali-denatured DNA. Comparison with the known sequence of this plasmid DNA reveals that the sequence derived from alkali-denatured DNA had 13 errors within the first 400 bases. For DNA treated with gene 6 exonuclease there is only one error within the first 500 bases, and only 4 errors within the first 540 bases. This performance rivals the best sequences obtained by any method using the ABI Model 373A, obtaining 540 nucleotides with over 99% accuracy.

EXAMPLE 8

Sequencing With a Modified Primer

The activity of Gene 6 exonuclease on phosphorothioate-containing DNA is minimal. For example, DNA synthesized using [α-$^{35}$S] dATP along with dCTP, dTTP and dGTP, produces DNA with phosphorothioate linkages on the 5' side of each adenine base. When this DNA is treated with varying amounts of Gene 6 exonuclease and T7 DNA polymerase for 5 min. at 37° C. in the presence of $MgCl_2$, and acid-precipitable radioactivity measured, the exonuclease activity present in 0.01 units of T7 DNA polymerase degrades more than 85% of the labeled DNA, but 1 unit of Gene 6 exonuclease is unable to cause cleavage of this DNA in the presence of the substitution of sulfur for oxygen in the phosphodiester linkage.

Referring to FIGS. 12A and 12B, T7 gene 6 exonuclease can be used with a modified primer for sequencing PCR products. FIG. 12A shows the scheme of example 5 for sequencing the products of PCR. FIG. 12B shows the proposed alternative. One normal (oxygen-only) primer is used, and one modified primer is used. The modified primer contains one or more phosphorothioate linkages (substituting sulfur for oxygen). The PCR results in product DNA which contains these primers.

Treatment of these primer extension products with gene 6 exonuclease results in degradation of only one strand. This allows the sequencing of one entire PCR product strand. If the PCR product is of typical size, i.e., less than 400 base pairs, it can potentially be sequenced using just 1 primer.

Other embodiments are within the following claims.

I claim:

1. A method for determining the nucleotide base sequence of a linear duplex DNA molecule, comprising the steps of:

providing said linear duplex DNA molecule by amplifying a desired nucleic acid by contacting said desired nucleic acid with two amplification primers, one which binds in a 5' region of said nucleic acid and one which binds in a 3' region of said nucleic acid, in the presence of a DNA polymerase and four dNTPS, contacting the linear duplex DNA molecule with a T7-type gene 6 exonuclease to allow said exonuclease to remove at least portion of said first strand of the DNA to allow extension of said second strand by a polymerase, providing a hybridization primer which hybridizes with said second strand of the DNA complementary to said portion of said first strand, and contacting the hybridization primer with said second strand of the DNA in the presence of at least one dNTP, at least one chain terminating agent, and a DNA polymerase, to allow said primer to be extended by said polymerase until extension is stopped by incorporation of the chain terminating agent, wherein one of the said amplification primers comprises one or more phosphorothioate linkages.

* * * * *